United States Patent [19]

Rydell et al.

[11] Patent Number: 4,919,121
[45] Date of Patent: Apr. 24, 1990

[54] INFLATION DEVICE FOR ANGIOPLASTY CATHETER

[75] Inventors: Mark A. Rydell, Golden Valley; Rick L. Shockey, Eagan, both of Minn.

[73] Assignee: Schneider (USA) Inc., A Pfizer Company, Minneapolis, Minn.

[21] Appl. No.: 306,047

[22] Filed: Feb. 6, 1989

[51] Int. Cl.$^5$ .............................................. A61M 29/00
[52] U.S. Cl. ........................................ 604/97; 604/99
[58] Field of Search ........................... 604/97–99, 604/207–211; 128/344, 348.1; 222/389–391; 401/172, 176; 433/89, 90

[56] References Cited

U.S. PATENT DOCUMENTS

| | | | |
|---|---|---|---|
| 4,370,982 | 2/1983 | Reilly | 604/98 |
| 4,413,989 | 11/1983 | Schjeldahl et al. | 604/96 |
| 4,439,185 | 3/1984 | Lundquist | 604/99 |
| 4,583,974 | 4/1987 | Kokernak | 604/99 |
| 4,655,749 | 4/1987 | Fischione | 604/98 |
| 4,723,938 | 2/1989 | Goodin et al. | 604/99 |
| 4,758,223 | 7/1988 | Rydell | 128/344 |
| 4,832,692 | 5/1989 | Box et al. | 604/99 |

*Primary Examiner*—C. Fred Rosenbaum
*Assistant Examiner*—William Lewis
*Attorney, Agent, or Firm*—Haugen and Nikolai

[57] ABSTRACT

A hand-operated inflator device for inflating the expander on a balloon-type catheter. It comprises a molded plastic housing for retaining a syringe tube therein for containing an inflation fluid. The housing also includes an internally threaded surface. A syringe plunger having an internal longitudinal bore and a longitudinal slot formed through the wall thereof has a piston mounted on the distal end for insertion into the syringe body. Fitted into the longitudinal slot is an externally threaded member which can be raised and lowered in a radial direction by manipulation of a manuable actuable means positioned in the longitudinal bore of the plunger. When the externally threaded member is raised, its teeth mesh with the teeth on the internally threaded annular surface of the housing, but when lowered, the threaded surfaces are disengaged. When the two are engaged, the piston is advanced in the syringe tube by rotating the plunger. When the two are disengaged, the plunger may be advanced by longitudinal force applied to the end of the plunger.

8 Claims, 1 Drawing Sheet

U.S. Patent   Apr. 24, 1990   4,919,121
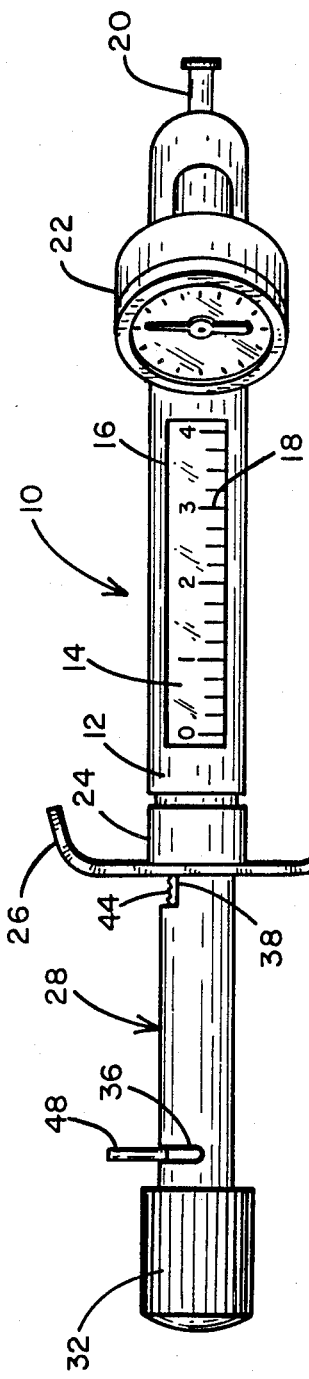
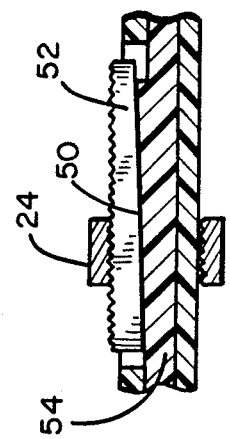
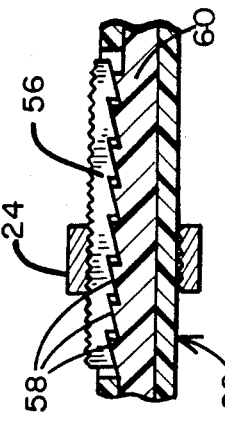
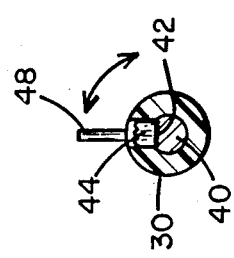
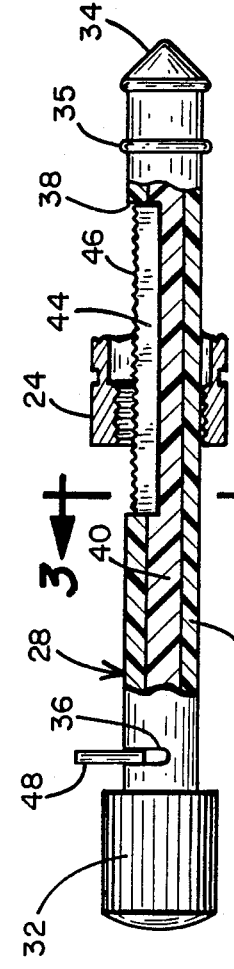
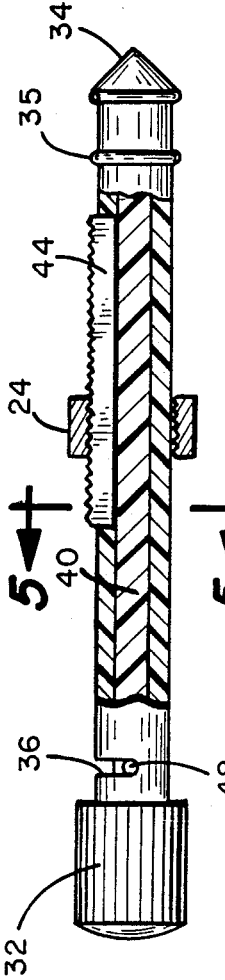
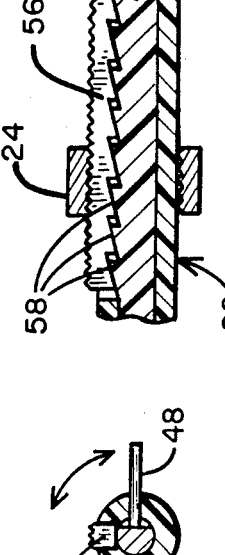

INFLATION DEVICE FOR ANGIOPLASTY CATHETER

BACKGROUND OF THE INVENTION

I. Field of the Invention

This invention relates generally to apparatus for performing angioplasty procedures for opening partially occluded blood vessels, and more particularly to a hand-operated inflation and fluid dispensing device adapted to be connected to the proximal end of an angioplasty catheter for either inflating the expander member on the catheter or supplying a radiopaque contrast medium through the catheter and out its distal end.

II. Discussion of the Prior Art

There is described in the Schjeldahl et al U.S. Pat. No. 4,413,989 the configuration of an angioplasty catheter specifically adapted to treat stenotic lesions located in one of the coronary arteries. Basically, the catheter comprises an elongated tubular member having a non-distensible expander member disposed proximate its distal end, the expander member being inflatable by introducing a fluid through the proximal end of the catheter whereby it flows through the lumen of the catheter and out one or more ports in the side wall of the tubular member which is surrounded by the expander member.

In treating stenotic lesions, it is often necessary to pressurize the expander member to a pressure in the range of from 7 to 10 atmospheres or more. This pressure must be sustained for periods of up to 30 seconds or more.

There is currently on the market an angioplasty catheter inflation device in the form of a molded plastic housing configured to contain a hypodermic-type syringe having a diameter of about 6.5 cms. and whose output port is coupled to the proximal end of the tubular catheter body. The plunger of the syringe is suitably positioned relative to integrally molded finger grips on the housing so that the plunger will fit in the palm of the hand as the user's fingers warp about the finger grips. By squeezing, fluid is ejected from the syringe and through the elongated catheter so as to inflate the expander member. The device is constructed in accordance with the Lundquist U.S. Pat. No. 4,439,185 assigned to Advanced Cardiovascular Systems, Inc. of Mountain View, Calif. Using this prior art device, however, it is extremely difficult for the cardiologist or technician to sustain the necessary pressures for the time interval during which the expander is pressurized. It requires a very strong grip and often it is difficult to hold the device steady, and at the desired inflation pressure due to the strong force which must be applied to the inflation device. While the applied force can be reduced by reducing the overall diameter of the syringe's piston, this necessarily reduces the volume of fluid available to, for example, initially fill the lumen of the catheter and the expander with fluid or to later inject contrast media when the site being treated is to be inspected using fluoroscopic techniques.

Other prior art angioplasty balloon catheter inflation devices are described in the Rydell U.S. Pat. No. 4,758,223 which is assigned to the assignee of the present application. The devices disclosed in that patent incorporate a pair of syringes, one with a large diameter piston which can be used to conveniently fill an angioplasty catheter and a second, small diameter piston which, actuated following the filling operation, can be used to create a relatively high pressure. While the devices shown in the Rydell patent can effectively be used by a cardiac surgeon in inflating and deflating a ballon angioplasty catheter, they required the manipulation of two separate pistons, thus requiring a certain amount of dexterity. Efforts have continued to develop and inflation device which is more simple to use in an operating room setting where quickness and dexterity are all-important.

SUMMARY OF THE INVENTION

In accordance with the present invention, both the filling operation and the application of high pressure can be obtained using only a single syringe plunger within a single syringe body. The syringe plunger is generally cylindrical and includes a resilient, elastomeric piston on its distal end. A longitudinal bore is formed within the plunger rod and, furthermore, a longitudinal slot is also formed through the wall of the plunger rod to meet with the longitudinal bore. Fitted into this slot is an externally threaded member which can be selectively raised or lowered in a radial direction to become engaged with or disengaged from an internally threaded ring surface formed on the syringe housing. Fitted into the longitudinal bore of the plunger is a device for effecting the raising and lowering of the externally threaded member. When the two threaded surfaces are disengaged, the plunger can be pressed longitudinally into or drawn longitudinally back from the syringe body by pressing or pulling on a knob joined to the proximal end of the syringe plunger. However, when the externally threaded member is brought into engagement with the internally threaded ring surface in the syringe housing, the plunger rod becomes effectively latched against pure translational displacement so that now a rotation of the plunger rod in the clockwise direction is needed to advance the piston into the syringe body while a counterclockwise rotation will withdraw the piston in the proximal direction.

Two separate mechanisms are disclosed for effecting the radial movement of the externally threaded member within the longitudinal slot formed in the housing. In one arrangement, a cylindrical rod having a cam surface thereon is disposed in the longitudinal bore of the plunger and when rotated by a conveniently-located thumb lever, will raise or lower the externally threaded member. In an alternative arrangement, a longitudinally displaceable rod having a ramp surface thereon is made to cooperate with a mating ramp surface on the underside of the externally threaded member. Longitudinal displacement of that rod, then, will produce radial movement of the externally threaded member.

OBJECTS

It is accordingly a principal object of the present invention to provide an improved inflation device for use with a balloon angioplasty catheter.

Another object of the invention is to provide an inflation device for a balloon angioplasty catheter which can be used to inject and aspirate an inflation fluid from the angioplasty catheter and to create and maintain a desired high pressure within the balloon of that catheter.

Yet another object of the invention is to provide an inflation device for an angioplasty catheter having convenient controls for causing the inflation and deflation of the balloon.

These as well as other objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 1 is a side elevation of the inflation device in accordance with the present invention.

FIG. 2 is a partial cross-sectional view of the plunger portion of the inflation device of FIG. 1 when disengaged from the syringe housing.

FIG. 3 is a cross-sectional view taken along the line 3—3 in FIG. 2.

FIG. 4 is a partial cross-sectional view of the syringe plunger when engaged with the syringe housing.

FIG. 5 is a cross-sectional view taken along the line 5—5 in FIG. 4.

FIG. 6 is a fragmentary cross-sectional view in accordance with another embodiment of the invention.

FIG. 7 illustrates by means of a further fragmentary drawing an alternative to the embodiment of FIG. 6.

DESCRIPTION OF THE PREFERRED EMBODIMENT

With reference to FIG. 1, there is indicated generally by numeral 10 an inflation device for use with a transluminal angioplasty balloon catheter. It comprises a syring housing 12 which surrounds a syring tube 14 which may typically have a volume of 10 to 20 cc. The syringe housing is preferably formed from a suitable plastic in a molding process and includes a window 16 through which graduated markings 18 on the syringe tube may be viewed. The distal end of the housing 12 has an opening through which the fluid outlet of the syringe tube 14 may project and it is provided with a luer fitting 20 to facilitate its connection to a mating fitting on an angioplasty catheter (not shown). The molded plastic housing 12 further supports a pressure gauge 22 which is in fluid communication with the syringe's outlet port and thus provides a means whereby the hydraulic pressure within the angioplasty catheter can be measured.

Integrally molded with the syringe housing 12 at its proximal end is a ring segment 24 which, as shown in the partially section view of FIG. 2 is provided with screw threads on its internal surface.

The radial extensions 26 integrally molded at the proximal end of the ring portion 24 serve as finger grips for the forefinger and index finger of the user.

Fitting into the open distal end of the housing 12 and passing through the ring portion 24 thereof is a syringe plunger 28. It can be seen in FIG. 2, it comprises an outer tubular member 30 having a knob 32 on its proximal end and a piston member 34 on its distal end. The piston member 34 is preferably formed from a suitable elastomeric material so that when inserted into the bore of the syringe tube 14, it will cooperate with the side walls of the syringe tube to form a generally fluid-tight seal therebetween. One or more O-rings, as at 35, may also be used to provide a good seal while allowing axial displacement of the piston plunger within the syringe tube 14.

The outer tubular portion 30 of the syringe plunger 28 has an arcuate radial slot 36 formed through the wall thickness thereof near the knob 32. It also includes a longitudinal slot 38 of a width defined by a radial arc of approximately 20' to 45°. Fitted within the internal bore of the plunger rod 30 is a cylindrical rod 40 having a flattened surface 42 formed thereon at a location along its length corresponding to the zone occupied by the longitudinal slot 38 in the wall of the tubular portion 30 when the plunger is disposed in the syringe tube 14. Fitted into the slot 38 is an externally threaded rack member 44 whose teeth 46 have the same pitch as the internal threads formed on the inner annular surface of the ring portion 24 of the housing 12.

Affixed to the rod 40 contained within the internal bore of the plunger 28 is a thumb lever 48 which passes through the radial slot 36. Thus, by manually actuating the thumb lever 48, the cam rod 40 may be rotated to raise and lower the externally threaded rack member 44 within the slot 38. The view of FIGS. 2 and 3 show the rack in its lowered position where the teeth 46 thereof are disengaged from the internal threads on the ring 24. In FIG. 4, the thumb lever 48 has been rotated within the slot 36 and, as can best be seen in FIG. 5, in doing so, the rack 44 is elevated into engagement with the internally threaded surface of the ring 24.

It can be seen, then, that when the threaded surfaces are disengaged, the surgeon may loop the forefinger and index finger of one hand around the finger grips 26 with the palm of the hand engaging the proximal end of the knob 32. By applying a squeezing force, he can move the plunger rod 28 into the syringe tube 14 and, in doing so, will force an inflation fluid through the outlet port 20 of the inflation device and into the angioplasty catheter (not shown). Once the catheter and the balloon have been filled and the balloon expanded to a predetermined pressure below the desired operating pressure, as indicated by gauge 22, the physician may readily manipulate the lever rod 48 with his thumb and, in doing so, cam the externally athreaded rack member 44 into engagement with the internal threads on the ring portion 24 of the syringe housing 12. The surgeon may now relax his grip on the device and the pressure will be maintained. When it is desired to increase the pressure to a desired working pressure, it can be done by merely rotating the knurled knob 32 to advance the piston 34 in the distal direction. The surgeon may also decrease the pressure, if desired, by rotating the knob in the opposite direction.

When the surgeon desires to deflate the balloon, he need merely flip the lever 48 back to the position shown in FIGS. 2 and 3 and, in doing so, the externally threaded rack 44 will disengage from the threaded surface on the ring 24 allowing the knob 32 to be pulled rearward, creating a vacuum in the syringe for aspirating the fluid from the catheter.

Referring to FIG. 6, there is shown an alternative to the rotatable cam rod 40 illustrated in FIGS. 2 through 5. In this arrangement, the undersurface 50 of the externally threaded member 52 is tapered and a longitudinally displaceable rod 54 having a mating ramp surface thereon is substituted for the rotatable cam 40 of the previous embodiment. The end of the rod 54 may project outwardly from the proximal end of the knob 32 so that it can be gripped by the surgeon and moved in the distal direction to raise the externally threaded member 52 in the slot 38 or moved proximally to lower the externally threaded member 52 out of engagement with the internal threads on the ring 24.

The arrangement shown in FIG. 7 is a variation of the arrangement shown in FIG. 6. Rather than having one continuous ramp surface, the undersurface of the externally threaded rack member 56 is provided with a plurality of short ramps 58 whose slopes are somewhat greater than the slope of the ramp surface 50 in FIG. 6. Again, the externally threaded member 56 is raised and lowered relative to the threaded ring 24 by an axial or longitudinal movement of the rod 60 contained in the longitudinal bore of the plunger rod 28. Using this approach, a shorter longitudinal stroke of the rod 60 is needed to engage and disengage the two threaded surfaces than may be required when the single ramp approach of FIG. 6 is used.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished withut departing from the scope of the invention itself.

What is claimed is:

1. An inflation device for a transluminal angioplasty catheter of the type including an elongated, flexible plastic tube having a proximal end and a distal end, said distal end supporting an expander member thereat, said inflation device comprising:
    (a) a syringe housing for retaining a tubular syringe body therein, said syringe body having a piston receiving bore, a fluid outlet port at its distal end, and means for coupling said oulet port to the proximal end of said catheter, said syringe housing including an internally threaded annular surface at the proximal end thereof, said annular surface being of a predetermined internal diameter;
    (b) a syringe plunger having a proximal end, a distal end and a piston member on said distal end of said plunger, said plunger being insertable into said piston receiving bore of said syringe body and having a longitudinally extending bore with a longitudinal slot formed through the wall of said cylindrical plunger extending from said longitudinal bore to the exterior of said cylindrical plunger, the outer diameter of said cylindrical plunger being less than said predetermined internal diameter of said annular surface on said plunger housing and a piston member on said distal end of said plunger;
    (c) an externally threaded member disposed in said longitudinal slot for radial movement between a first position wherein the threads on said externally threaded member are out of engagement with said internally threaded annular surface and a second position where said threads on said externally threaded member engage said internally threaded annular surface; and
    (d) manually actuable means disposed in said longitudinal bore in said plunger for selectively moving said externally threaded member between said first and second positions, whereby rotation of said syringe plunger within said syringe housing produces axial movement of said piston within said piston receiving bore when said externally threaded member is in said second position.

2. The inflation device as in claim 1 wherein said syringe housing includes a longitudinal window for viewing graduation markings on said syringe body.

3. The inflation device as in claim 1 and further including finger grip means affixed to said syringe housing.

4. The inflation device as in claim 1 and further including gauge means mounted on said syringe housing and in fluid communication with said outlet port for monitoring hydraulic pressure within said catheter.

5. The inflation device as in claim 1 wherein said manually actuable means comprises a rotatable cam disposed in said longitudinal bore in said plunger and cooperating with said externally threaded member.

6. The inflation device as in claim 5 and further including a radially projecting lever affixed to said rotatable cam and extending through a circumferential slot formed through the wall of said cylindrical plunger near the proximal end thereof.

7. The inflation device as in claim 1 wherein said externally threaded member includes a ramp on the undersurface thereof and said manually actuable means comprises a longitudinally movable member disposed in said longitudinal bore in said plunger and having a ramp surface thereon for engaging said ramp on the undersurface of said externally threaded member.

8. The inflation device as in any one of claims 1 through 7 and further including a knurled knob disposed on the proximal end of said syringe plunger for facilitating the manual rotation of said plunger within said syringe body when the externally threaded member is in said second position.

* * * * *